US010487027B2

(12) United States Patent
Laroche et al.

(10) Patent No.: US 10,487,027 B2
(45) Date of Patent: Nov. 26, 2019

(54) ZEOLITIC ABSORBENTS COMPRISING A ZEOLITE WITH HIERARCHICAL POROSITY (71) Applicants: IFP ENERGIES NOUVELLES, Rueil-Malmaison (FR); Arkema France, Colombes (FR)

(72) Inventors: Catherine Laroche, Vernaison (FR); Ludivine Bouvier, Orthez (FR); Cecile Lutz, Gan (FR); Arnaud Baudot, Vernaison (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 15/501,741

(22) PCT Filed: Aug. 4, 2015

(86) PCT No.: PCT/EP2015/067967
§ 371 (c)(1),
(2) Date: Feb. 3, 2017

(87) PCT Pub. No.: WO2016/020387
PCT Pub. Date: Feb. 11, 2016

(65) Prior Publication Data
US 2017/0217858 A1 Aug. 3, 2017

(30) Foreign Application Priority Data
Aug. 5, 2014 (FR) ...................... 14 57624

(51) Int. Cl.
| B01J 20/18 | (2006.01) |
| C07C 7/13 | (2006.01) |
| B01J 20/28 | (2006.01) |
| B01J 20/12 | (2006.01) |
| B01J 20/30 | (2006.01) |
| B01D 15/18 | (2006.01) |

(52) U.S. Cl.
CPC ............ *C07C 7/13* (2013.01); *B01D 15/1828* (2013.01); *B01J 20/12* (2013.01); *B01J 20/18* (2013.01); *B01J 20/183* (2013.01); *B01J 20/186* (2013.01); *B01J 20/2803* (2013.01); *B01J 20/28004* (2013.01); *B01J 20/2808* (2013.01); *B01J 20/28011* (2013.01); *B01J 20/28019* (2013.01); *B01J 20/28059* (2013.01); *B01J 20/28069* (2013.01); *B01J 20/28078* (2013.01); *B01J 20/28083* (2013.01); *B01J 20/28085* (2013.01); *B01J 20/28088* (2013.01); *B01J 20/28092* (2013.01); *B01J 20/3007* (2013.01); *B01J 20/3028* (2013.01); *B01J 20/3042* (2013.01); *B01J 20/3078* (2013.01); *B01D 15/1821* (2013.01)

(58) Field of Classification Search
CPC ...... B01J 20/3078; B01J 20/18; B01J 20/183; B01J 20/186; B01J 20/12; B01J 20/2803; B01J 20/28069; B01J 20/28092; B01J 20/28004; B01J 20/28078; B01J 20/28011; B01J 20/28019; B01J 20/28059; B01J 20/2808; B01J 20/28083; B01J 20/28085; B01J 20/28088; B01J 20/3028; B01J 20/3042; B01J 20/3007
USPC ............ 502/60, 63, 64, 68, 69, 79, 407, 414
See application file for complete search history.

(56) References Cited

U.S. PATENT DOCUMENTS

| 2,985,589 | A |   | 5/1961  | Broughton et al. |
| 3,558,730 | A |   | 1/1971  | Neuzil |
| 3,663,638 | A |   | 5/1972  | Neuzil |
| 3,878,127 | A | * | 4/1975  | Rosback ............... B01J 20/186 423/112 |
| 3,960,774 | A | * | 6/1976  | Rosback ............... B01J 20/186 502/79 |
| 5,284,992 | A |   | 2/1994  | Hotier et al. |
| 5,629,467 | A |   | 5/1997  | Hotier et al. |
| 7,452,840 | B2|   | 11/2008 | Plee et al. |
| 7,785,563 | B2|   | 8/2010  | Ryoo et al. |
| 7,812,208 | B2|   | 10/2010 | Cheng et al. |
| 7,820,869 | B2|   | 10/2010 | Priegnitz et al. |
| 8,283,274 | B2|   | 10/2012 | Cheng et al. |
| 8,530,367 | B2|   | 9/2013  | Bouvier et al. |
| 8,735,643 | B2|   | 5/2014  | Bouvier et al. |
| 9,744,519 | B2|   | 8/2017  | Lutz et al. |
| 2005/0170947 | A1 |  | 8/2005  | Plee et al. |
| 2009/0326308 | A1 |  | 12/2009 | Kulprathipanja et al. |
| 2010/0155303 | A1 |  | 6/2010  | Toida et al. |
| 2010/0196213 | A1 |  | 8/2010  | Lutz et al. |
| 2011/0011804 | A1 |  | 1/2011  | Cheng et al. |
| 2011/0105301 | A1 |  | 5/2011  | Wang et al. |
| 2013/0012377 | A1 |  | 2/2013  | Suh et al. |
| 2016/0207025 | A1 |  | 7/2016  | LaRoche et al. |

FOREIGN PATENT DOCUMENTS

| CN | 1267185 C      | 8/2006  |
| FR | 3010328 A1     | 3/2015  |
| FR | 3010402 A1     | 3/2015  |
| JP | 52027790 A     | 3/1975  |
| JP | 2007238484 A   | 9/2007  |
| JP | 2002537109 A   | 11/2007 |
| JP | 2010529939 A   | 9/2010  |
| JP | 2012502993 A   | 2/2012  |
| JP | 2012533427 A   | 12/2012 |
| WO | 2007015391 A1  | 2/2007  |
| WO | 2007043731 A1  | 4/2007  |
| WO | 2008009845 A1  | 1/2008  |
| WO | 2008152319 A2  | 12/2008 |
| WO | 2010033277 A1  | 3/2010  |
| WO | 2011011190 A2  | 1/2011  |
| WO | 2013106816 A1  | 7/2013  |
| WO | 2015032923 A1  | 3/2015  |

OTHER PUBLICATIONS

International Search Report and Written Opinion for International Application No. PCT/EP2015/067967, dated Oct. 28, 2015—13 Pages.

(Continued)

*Primary Examiner* — Elizabeth D Wood
(74) *Attorney, Agent, or Firm* — RatnerPrestia (57) ABSTRACT

The invention relates to zeolitic absorbents based on at least one zeolite with hierarchical porosity, containing barium or barium and potassium, to the uses thereof for separating para-xylene from aromatic fractions containing 8 carbon atoms, and to the method for separating para-xylene from aromatic fractions containing 8 carbon atoms.

20 Claims, 1 Drawing Sheet

(56) References Cited

OTHER PUBLICATIONS

E.P. Barrett, et al.. "The Determination of Pore Volume and Area Distributions in Porous Substances .I. Computations from Nitrogen Isotherms", J. Am. Chem. Soc., vol. 73, No. 1, 1951, pp. 373-380.
D. Verborkend et al., Hierarchical Y and USY Zeolites Designed by Post-Synthetic Strategies, Adv. Funct. Mater., 22, 2012, pp. 916-928.
Japanese Notice of Rejection for Japanese Application No. 2017-506340, dated May 14, 2019 with translation, 12 pages.

* cited by examiner

ZEOLITIC ABSORBENTS COMPRISING A ZEOLITE WITH HIERARCHICAL POROSITY

CROSS-REFERENCE TO RELATED APPLICATIONS

This is the national phase of International Application No. PCT/EP2015/067967, filed 4 Aug. 2015, which claims priority to French Application No. 1457624, filed 5 Aug. 2014. The disclosure of each of these applications is incorporated herein by reference in its entirety for all purposes.

FIELD OF INVENTION

The invention relates to zeolite adsorbents comprising zeolites with hierarchical porosity which may be used in the field of separating xylene isomers, and in particular separating para-xylene from a mixture of C8 aromatic hydrocarbons predominantly containing ortho-, meta- and para-xylene, ethylbenzene and the like.

BACKGROUND OF THE INVENTION para-Xylene is one of the major intermediates of petrochemistry. It is transformed into terephthalic anhydride or acid or into methyl terephthalate, and then subsequently polycondensed with diethylene glycol, for example. The polyester PET obtained is then converted into synthetic fibres or resins intended especially for the textile industry, for packaging drinks, and the like.

para-Xylene is generally separated from the other C8 aromatic isomers either by crystallization or by industrial chromatography also known as separation by simulated moving bed adsorption. The technique of separation by crystallization today represents less than 20% of the total production of para-xylene, whereas separation by simulated moving bed adsorption today represents about 80% to about 85% of this production of para-xylene. Finally, about 2% of the total production of para-xylene originates from the combination of the two abovementioned technologies, in which crystallization is used as the finishing step.

Industrial chromatography separation techniques are performed in liquid phase or in gas phase, but separation by industrial chromatography is most generally performed in liquid phase.

Simulated moving bed separation is understood here in the broad sense, i.e. it may be either a simulated counter-current, or a simulated co-current, or a "Varicol" process. The common feature to this family of processes is that the solid adsorbent is used in a fixed bed, and the flows, which are liquid or optionally gaseous in contact with the adsorbent, are governed either by means of a set of on-off valves, or by means of a complex single valve known as a rotary valve.

When the active element of the solid adsorbents used as adsorption agents in these processes is a zeolite, it is obtained in the form of powder (crystals), and preferably used at the industrial scale in the form of agglomerates. These zeolite adsorbents, agglomerated in the form of platelets, beads or extrudates, generally consist of a zeolite powder, which constitutes the active element as regards the adsorption and of a binder intended to ensure the cohesion of the crystals in the form of beads or extrudates, generally known as grains.

This binder also gives the grains sufficient mechanical strength to withstand the mechanical stresses to which they are subjected during their use in units. These mechanical stresses are the cause of the formation of fines, which bring about a deterioration in performance during the operating time of the process.

The processes for separating xylenes in a simulated moving bed (SMB) have undergone numerous technological improvements in recent decades, especially as regards the fluid distribution plateaux, but relatively few changes regarding the particle size characteristics of the solid adsorbent.

The prior art documents describing the chemical and microscopic characteristics of the zeolite adsorbents used for separation of para-xylene are particularly abundant, and mention may be made, for example, by way of illustration, of patents U.S. Pat. Nos. 3,558,730, 3,663,638, 3,960,774, 7,820,869, 7,812,208, 8,283,274, 8,530,367 and 8,735,643.

The general teaching regarding the chemical characteristics of these solid adsorbents is that it is necessary to use a zeolite of faujasite structure (zeolite LSX, X or Y) and in which the compensating ions are in major amount $Ba^{2+}$ ions or in major amount $Ba^{2+}$ ions and in minor amount $K^+$ ions.

In addition, the general teaching regarding the microscopic characteristics of the adsorbent is that zeolite X crystals preferably less than 1.6 µm in size (number-average diameter) may be used. Some of the most recent documents teach the use of adsorbents based on zeolite X crystals less than 0.5 µm in size (US 2009/326 308) or between 0.1 µm and 0.4 µm in size (CN1267185C), in order to improve the performance of the process for separating xylene isomers due to a gain in material transfer of these adsorbents compared with the conventional adsorbents mentioned above.

Moreover, in the field of catalysis, especially in hydrocracking processes, when zeolite supports are used, it is common practice to seek to improve the accessibility of the molecules to the micropores of said zeolites by creating mesopores in the zeolite FAU (zeolite Y) crystals by post-synthesis treatment.

The studies by Inayat et al. (Angew. Chem. Int. Ed., (2012), 51, 1962-1965) teach that it is possible to synthesize mesoporous zeolite X crystals. It may thus be expected that the accessibility to the micropores is improved relative to that of conventional X crystals. Consequently, a person skilled in the art would be inclined to wish to use such mesoporous zeolite X crystals to form efficient adsorbents for the separation of xylene isomers.

However, this publication (Inayat, ibid.) shows a 23% loss of the micropore volume of the synthesized mesoporous zeolite NaX, relative to that of conventional zeolite NaX. This is in total contradiction with a selective adsorption volume that is as large as possible, which is desired for the adsorbents used in the separation of xylene isomers.

The observation cannot be avoided that, between the hypothetical gain in material transfer and the confirmed loss of micropore volume, it is impossible to predict the performance of an adsorbent prepared with mezoporous zeolite X crystals for the separation of xylene isomers.

On the other hand, the general teaching concerning the macroscopic characteristics of the adsorbent is that the content of active material can be increased, by transforming the binder into zeolite under the action of a basic alkaline solution, such that the finished product contains a reduced amount of non-zeolitic phase, which may be quantified by reference to an adsorbent composed solely of zeolite, in powder form, from adsorption measurements or from XRD peak intensities. This transformation of the binder into active material for the purposes of adsorption moreover makes it possible to maintain the mechanical strength of the agglomerate (U.S. Pat. No. 8,530,367), which is necessary for withstanding the mechanical stresses during their use in units.

The prior art documents precisely describing the granulometric and morphological characteristics of zeolite adsorbents in association with the distribution plateaux technology of the simulated moving bed process are much rarer and markedly less precise. At the present time, a person skilled in the art does not appear especially to have available any document teaching how to select the optimum particle size characteristics of adsorbents as a function of the properties of the zeolite X crystals used to form the adsorbent.

Some of the documents mentioned previously (for example U.S. Pat. Nos. 3,960,774, 7,812,208, US 2009/326 308) mention the usual agglomeration techniques (extrusion optionally followed by crushing, agglomeration in a frustoconical mixer, for example Nautamix®, in a granulating drum, spheronizator) for obtaining adsorbents in the form of extrudates, spheres or beads in the particle size category ranging from 0.25 mm to 1.2 mm (16-60 standard US mesh size), irrespective of the diameter of the zeolite X crystals used in the adsorbent. In Example 1 of US 2011/105 301, the authors disclose adsorbents in agglomerated form, obtained by agglomeration in a granulating drum ("tumbling") followed by screening in the particle size category ranging from 0.35 mm to 0.8 mm.

In these documents, the numerical indications regarding the particle sizes of the adsorbents correspond in practice to the mesh aperture of the two gauzes used for selecting the agglomerates, i.e. they correspond to the lower and upper limits of the smallest and largest agglomerate of the distribution, but do not mention mean diameter values.

Patent CN1267185 stresses the importance of a narrow particle size distribution for improving the filling of adsorbents in industrial units: it discloses an adsorbent based on X crystals between 0.1 μm and 0.4 μm in size, in the form of particles with a diameter of between 0.35 mm and 0.8 mm, and satisfying the following distribution: 20% by weight to 25% by weight in the particle size category 0.60 mm to 0.80 mm, 50% by weight to 60% by weight in the particle size category 0.46 mm to 0.60 mm and 20% by weight to 30% by weight in the particle size category 0.35 mm to 0.46 mm.

Given that the particle size distributions of the agglomerates obtained via the standard forming techniques generally follow a lognormal law, a particle size distributed between 0.25 mm and 1.2 mm (for instance in U.S. Pat. No. 7,820,869 and US 2009/326 308) or between 0.35 mm and 0.8 mm (for example in US 2011/105 301) corresponds to a weight-average diameter for a distribution derived from screening of the agglomerates, which is in the region of the median values, namely at about from 0.55 mm to 0.65 mm, as a function of the standard deviation of the distribution.

U.S. Pat. No. 8,530,367 discloses only the number-average diameters of the adsorbents in the form of beads or extrudates, obtained by extrusion, compacting or agglomeration, namely a number-average diameter ranging from 0.4 mm to 2 mm and in particular from 0.4 mm to 0.8 mm, but no mention is made of the lower and upper limits of the smallest and largest agglomerate of the distribution. It is simply stated that the finest agglomerated particles may be removed by cycloning and/or screening and/or the particles that are too coarse by screening or crushing, in the case of extrudates, for example.

It should be noted that a number-average diameter of 0.4 mm corresponds to a higher volume-average diameter, typically from 0.45 mm to 0.55 mm depending on the standard deviation of the distribution, and similarly a number-average diameter of 0.8 mm would correspond to a volume-average diameter of about 0.9 mm to 1.0 mm. The examples of U.S. Pat. Nos. 7,452,840 and 8,530,367 disclose agglomerates with an equivalent diameter equal to 0.7 mm obtained by extrusion, which are subjected to crushing and screening, both for the agglomerates prepared from conventional zeolite X crystals of 2.1 μm and for the agglomerates prepared from zeolite X crystals with a diameter reduced to 1.6 μm.

Consequently, the prior art shows that, irrespective of the properties of the zeolite X crystals used in the adsorbents, the particle size of the adsorbents remains unchanged.

If reference is made to the theoretical expression of the resistance to material transfer as described by Ruthven in *Principles of Adsorption and Adsorption Processes*, p. 243, the size of the adsorbents is a parameter that it would optionally be sought to reduce in order to promote the material transfer since the diffusional resistance between the crystals (also known as the "macroporous resistance") is proportional to the square of the diameter of the adsorbents. However, the reduction of the size of the adsorbents is limited by the impact that this would then have during the use of the adsorbent in the industrial application, since the particle size of the adsorbents determines the pressure loss in the industrial unit and the uniformity of packing.

Moreover, it is known in the literature relating to concrete granulates that, for mixtures consisting of irregular-shaped particles having broad particle size distributions, the compactness reduces if the shape of the particles departs from sphericity. Moreover, the compactness increases with the spreading of the particle size distribution since the small particles can become lodged in the interstices created between the larger particles (Cumberland and Crawford, *The Packing of particles*, Elsevier, Amsterdam, (1987); German, *Introduction to particle packing in Powder packing characteristics*, (1989) pp. 1-20).

The compactness of the adsorbent bed, which it is desired to maximize in order to achieve maximum productivity with a given adsorbent, also depends on the mode of packing. The filling of the adsorbent in industrial units must be done as densely as possible so as to reduce as much as possible the void fraction left between the beads (Bed porosity: εb).

The difference between "loose" loading without taking particular care and "dense" loading is easily up to 10% of the bulk packing density (grams of adsorbent per $m^3$ of bed). A method of choice for performing dense loading consists in creating a homogeneous "rain" of adsorbent over the entire surface of the bed and in leaving the level to rise sufficiently slowly (several hours). Various commercial devices (Densicat®, Catapac®, Calipac®) exist for doing this. The principle consists in resuming a vertical flow at a controlled rate of adsorbent via a series of horizontal straps or wheels in rotation (at a precisely determined angular speed) so as to spray the adsorbent from the centre to the periphery.

Patent application WO 2008/152 319 describes agglomerates of controlled size and morphology and with very high sphericity obtained via a particularly advantageous forming technique, namely atomization. Said document shows that it is possible to obtain by atomization beads that are both sufficiently dense and mechanically strong and which have very good sphericity in a size range (mean diameter) from 50 μm to 600 μm and preferably from 50 μm to 500 μm. However, said document does not teach how to select the optimum characteristics (especially size and morphology) of the adsorbent as a function of the properties of the zeolite crystals.

It is moreover an ongoing aim to seek constantly to improve the production efficiency of the separation of para-xylene from aromatic fractions containing 8 carbon atoms. To achieve this aim, the abovementioned prior art teaches that one solution might be to improve the intragranular material transfer within the adsorbent, and to increase the amount of adsorbent per bed volume and to decrease the porosity of the bed, i.e. to have available a more compact and denser bed of adsorbent.

According to the theoretical expression of the material transfer resistance as described by Ruthven in *Principles of Adsorption and Adsorption Processes*, p. 243, one of the solutions for achieving this aim would also be to decrease the size of the zeolite adsorbent beads. However, one of the drawbacks directly linked to the ever greater reduction in size of the beads is a consequent increase in the loss of pressure. To compensate for the increase in the loss of pressure, it is necessary to increase the pressure that must be applied to the adsorbent beds and thus take the risk of breaking the zeolite adsorbents in the beds.

Thus, the prior art more preferentially recommends the solution which consists in further reducing the size of the zeolite crystals within zeolite adsorbents whose bead size (volume-average diameter) is not less than the value of the order of 0.5 mm.

There thus remains a need for zeolite adsorbents in the form of agglomerates comprising crystals of zeolite FAU of X type, in which the compensating ions are predominantly barium ions or barium and potassium ions, making it possible to further increase the production efficiency of para-xylene, without increasing the pressure loss in units for separating para-xylene in a simulated moving bed.

The term "predominantly" used above to characterize the compensating ions present in the type X zeolite means a molar amount of greater than 50% of ions relative to the total molar amount of ions present in the cationic sites of said type X zeolites. It should be understood that all the cationic sites of said zeolites X are occupied by a charged compensating cation, the zeolites used being electronically neutral during their use.

The need for even more efficient zeolite adsorbents in applications for the separation of para-xylene in a simulated moving bed described above may also be expressed by a need for zeolite adsorbents that would combine the following properties:
  selective adsorption volume of the zeolite adsorbent that is as large as possible per unit bed volume, i.e.:
    α) the largest possible zeolite content, zeolite constituting the microporosity within which the selective adsorption takes place;
    β) the smallest possible grain porosity (high grain density)
    γ) the smallest possible porosity of the adsorbent bed (high compactness)
  the fastest possible material transfer within the zeolite adsorbent, i.e. a minimum time for a hydrocarbon molecule to go from the exterior of the adsorbent to the core of the zeolite crystals of the zeolite adsorbent.

In other words, there is still a need for zeolite adsorbents that combine both optimum micropore transfer and improved macropore transfer while at the same time conserving a sufficient selective adsorption volume per unit bed volume so as to maximize the gain in productivity during their use in processes for separating para-xylene in separation units using the simulated moving bed technique.

SUMMARY OF THE INVENTION

It has now been found that the aims mentioned above may be achieved, totally or at least partially, by means of the zeolite adsorbents according to the invention described in the description that follows.

Specifically, the inventors have discovered, surprisingly, that the use of zeolite adsorbents obtained from zeolites with hierarchical porosity or "mesoporous" zeolites in the present invention makes it possible to further reduce the size (volume-average diameter) of the zeolite adsorbents, without leading to a substantial increase in pressure loss, and this being possible irrespective of the size of the zeolite crystals within said adsorbents and in particular for crystal sizes equal to the size of conventional crystals or larger, i.e. typically micrometric sizes, i.e. of the order of magnitude of a micrometer.

In other words, it has been discovered that it is possible to overcome all or at least some of the drawbacks noted in the prior art by performing a process for separating para-xylene using a zeolite adsorbent according to the invention whose particle size characteristics (volume-average diameter, particle size distribution and morphology) are such that they make it possible to maximize the bed compactness. These particle size characteristics lead to an adapted and optimum macropore transfer.

DETAILED DESCRIPTION OF CERTAIN EMBODIMENTS OF THE INVENTION

Thus, and according to a first aspect, the present invention relates to a zeolite adsorbent for which:
  the content of crystalline phase in the form of zeolite FAU of X type with hierarchical porosity is between 50% and 99% by weight and preferably from 80% to 98% by weight, relative to the total mass of the adsorbent;
  the content of barium ions ($Ba^{2+}$), expressed as barium oxide (BaO) is greater than 10%, preferably greater than 15%, very preferably greater than 20%, even more preferably greater than 23%, or even greater than 33% by weight relative to the total mass of the adsorbent, advantageously, the barium oxide content is between 23% and 42% and typically between 30% and 40% by weight relative to the total weight of the adsorbent;
  the content of potassium ions ($K^+$), expressed as potassium oxide ($K_2O$), is less than 25%, preferably between 0% and 20%, even more preferably between 0% and 15% and very preferably from 0% to 10% by weight relative to the total mass of the adsorbent; and
  the volume-average diameter is between 0.2 mm and 0.6 mm and preferably between 0.3 mm and 0.6 mm.

In a preferred embodiment, the zeolite adsorbent of the invention has an external surface area, measured by nitrogen adsorption (t-plot method described later), of greater than 20 $m^2.g^{-1}$, preferably greater than 30 $m^2.g^{-1}$, more preferably between 30 $m^2.g^{-1}$ and 200 $m^2.g^{-1}$ and more preferentially between 30 $m^2.g^{-1}$ and 150 $m^2.g^{-1}$.

According to another preferred embodiment, the zeolite adsorbent of the invention has an outer surface area, measured by nitrogen adsorption (t-plot method described later), of greater than 20 $m^2.g^{-1}$, preferably greater than 30 $m^2.g^{-1}$, more preferably between 30 m$^2$.g$^{-1}$ and 200 m$^2$.g$^{-1}$ and more preferentially between 30 m$^2$.g$^{-1}$ and 150 m$^2$.g$^{-1}$, said outer surface area being associated with a population of mesopores with a mean diameter of between 2 nm and 50 nm. The term "associated" in the preceding sentence indicates that the population of mesopores contributes towards the measured value of the outer surface area, in addition to the outer surface area of the zeolite crystals.

In the text hereinbelow, and unless otherwise indicated, the limits of a range of values are included in that range, especially in the expressions "between" and "from . . . to . . . ".

The term "zeolite with hierarchical porosity" means a zeolite containing both micropores and mesopores, in other words a zeolite that is both microporous and mesoporous. The term "mesoporous zeolite" means a zeolite whose microporous zeolite crystals have, in conjunction with the microporosity, internal cavities of nanometric size (mesoporosity), which are readily identifiable by observation using a transmission electron microscope (TEM), as described, for example, in U.S. Pat. No. 7,785,563.

Preferably, in the present invention, use will be made of a "zeolite with hierarchical porosity" or "mesoporous zeolite" having an outer surface area, defined by the t-plot method described later, of between 40 m$^2$.g$^{-1}$ and 400 m$^2$.g$^{-1}$, preferably between 40 m$^2$.g$^{-1}$ and 200 m$^2$.g$^{-1}$ and more preferably between 40 m$^2$.g$^{-1}$ and 150 m$^2$.g$^{-1}$.

In the present invention, the outer surface areas of the zeolite adsorbent or of the zeolite with hierarchical porosity are calculated via the t-plot method from the nitrogen adsorption isotherm at a temperature of 77 K, after degassing under vacuum (P<6.7×10$^{-4}$ Pa), at a temperature of between 300° C. and 450° C. for a time ranging from 9 hours and 16 hours and preferably at 400° C. for 10 hours.

The mean diameter of the mesopores is determined via the Barrett-Joyner-Halenda method (BJH method, E. P. Barrett, L. G. Joyner, P. P. Halenda, "The Determination of Pore Volume and Area Distributions in Porous Substances. I. Computations form Nitrogen Isotherms", *J. Am. Chem. Soc.*, 73(1), (1951), 373-380), from the absorption arm of the nitrogen physisorption isotherm at 77 K.

Advantageously, the mean diameter volume distribution thus determined for the mesopores of the adsorbent according to the invention, represented graphically by dV/dDm or dV/dlogDm as a function of the mean diameter Dm, corresponds to a narrow unimodal distribution.

The term "unimodal distribution" means a distribution having only one peak. A mean diameter unimodal distribution is thus characterized by a single peak, for which the mean diameter value at the top of the peak is known as the "mode" or alternatively the dominant value, and represents the most frequent value of the distribution. When a distribution has two peaks separated by a trough, the distribution is said to be bimodal. The invention does not relate to the case of bimodal or even multimodal distribution, i.e. distribution in which there are several zones of concentration of values separated by discontinuities. Such distributions are characteristic of the presence of several populations of pores with different mean diameters.

The term "narrow" used to characterize the mean diameter distribution of the mesopores indicates that the mid-height width of the distribution about the mode is less than 20 nm, preferably less than 15 nm, preferably between 10 nm and 0.1 nm and more preferably between 5 nm and 0.5 nm, as described later in the characterization techniques.

The crystals of the mesoporous zeolite(s) included in the zeolite adsorbent of the invention, alone or as a mixture with other identical or different, mesoporous or non-mesoporous zeolite crystals, are agglomerated with a binder. According to a preferred aspect of the invention, the binder content is as low as possible, so as to optimize the zeolite content of the zeolite adsorbent, but, however, sufficient to ensure the cohesion of the material.

The binder included in the zeolite adsorbent of the present invention is chosen from the conventional binders known to those skilled in the art, which may be zeolitizable or non-zeolitizable. This binder comprises, and preferably consists of, a clay or a mixture of clays. These clays are preferably chosen from kaolines, kaolinites, nacrites, dickites, halloysites, attapulgites, sepiolites, montmorillonites, bentonites, illites and metakaolins, and also mixtures of two or more thereo in all proportions.

In the present invention, the "binder" described above is an agglomeration binder which ensures the cohesion of the zeolite crystals in the zeolite adsorbent (or agglomerated zeolite material) of the invention. This binder also differs from the zeolite crystals in that they do not have a zeolitic crystalline structure after calcinations, which is the reason why the binder is often termed inert, and more precisely inert towards adsorption and ion exchange.

According to a particularly preferred aspect, the binder present in the zeolite adsorbent of the invention consists solely of one or more clays, and preferably of only one clay.

The zeolite adsorbent according to the present invention may also comprise one or more other components, in an amount of between 0 and 5%, preferably between 0 and 1% and more preferably between 0 and 0.5%, the percentages being expressed on a weight basis relative to the total weight of the zeolite adsorbent. This or these other component(s) are generally the residues of the additives, and other synthetic auxiliaries of said zeolite adsorbent.

Examples of such other components especially comprise ash of the additives after calcinations, silica, and the like. It should be understood that these other components are generally present in the form of residues or traces and are not used to provide any binding or cohesive nature to the zeolite adsorbents comprising at least one mesoporous zeolite of the invention.

The zeolite adsorbent of the present invention may be in various forms such as those that are well known to a person skilled in the art, who is a specialist in the agglomeration of powders or crystals, especially zeolite crystals, and, for example, and in a non-limiting manner, the zeolitic agglomerated material of the invention may be in the form of beads, yarn, extrudates or the like, and entirely preferably in the form of beads.

According to a preferred embodiment of the present invention, the zeolite adsorbent is in the form of zeolite agglomerates comprising zeolite X with hierarchical porosity and in which the compensating ions are predominantly barium or barium and potassium, said adsorbents having particular size and morphology characteristics relative to a conventional adsorbent.

The expression "predominantly barium or barium and potassium" means that the zeolite adsorbent has:
  a content of barium, expressed as barium oxide (BaO), of greater than 10%, preferably greater than 15%, very preferably greater than 20%, even more preferably greater than 23%, or even greater than 33% by weight relative to the total mass of the adsorbent; advantageously, the barium oxide content is between 23% and 42% and typically between 30% and 40% by weight relative to the total weight of the adsorbent, and a content of potassium, expressed as potassium oxide ($K_2O$), of less than 25%, preferably between 0 and 20%, even more preferably between 0% and 15% and very preferably from 0% to 10% by weight relative to the total mass of the adsorbent.

According to yet another preferred embodiment, the total content of alkali metal or alkaline-earth metal ions, other than barium and potassium, expressed as the total content of ions of alkali metal or alkaline-earth metal oxides other than barium oxide BaO and potassium oxide $K_2O$, is between 0 and 5% relative to the total mass of the adsorbent.

As indicated previously, use of the present invention advantageously involves a zeolite adsorbent having particular size and morphology characteristics relative to a conventional adsorbent.

Specifically, it has been discovered, surprisingly, that, relative to an agglomerate with a mean volume diameter of 0.7 mm comprising zeolite X with hierarchical porosity, the productivity is improved by selecting a form of beads in which the mean diameter may be further reduced without, however, significantly increasing the loss of pressure.

Thus, besides the mean volume diameter of between 0.2 mm and 0.6 mm and preferably between 0.3 mm and 0.6 mm, the zeolite adsorbent of the invention is advantageously in the form of beads, and preferably in the form of beads whose sphericity characteristics are such that:
- the mean bluntness is between 70% and 100%, preferably between 80% and 100%, preferably between 85% and 100% and even more preferably between 90% and 100%;
- the percentage of particles having an elongation of 0% is between 5 and 100, preferably between 10 and 100 and preferably between 25 and 100.

According to a preferred embodiment, the zeolite adsorbent of the invention also has the following sphericity characteristic: the percentage of the particles with an elongation of less than 10% is between 50 and 100, preferably between 70 and 100 and preferably between 80 and 100.

The methods for measuring the sphericity are well known to those skilled in the art and are described later in the characterization techniques.

The zeolite adsorbent of the present invention has an outer surface area, measured by nitrogen adsorption, of greater than 20 $m^2.g^{-1}$, preferably greater than 30 $m^2.g^{-1}$, more preferably between 30 $m^2.g^{-1}$ and 200 $m^2.g^{-1}$ and more preferentially between 30 $m^2.g^{-1}$ and 150 $m^2.g^{-1}$.

According to yet another preferred embodiment, the zeolite adsorbent according to the invention has an Si/Al atomic ratio of between 1.00 and 2.00, preferably between 1.00 and 1.80, more preferably between 1.15 and 1.80 and even more preferably between 1.15 and 1.60.

The zeolite adsorbent of the invention preferably has a grain density of between 1.0 $g.cm^{-3}$ and 1.4 $g.cm^{-3}$ and preferably between 1.1 $g.cm^{-3}$ and 1.3 $g.cm^{-3}$ as measured by mercury intrusion (relative to the dry mass of the zeolite adsorbent) and a total volume contained in the macropores and mesopores (sum of the macropore volume and of the mesopore volume) measured by mercury intrusion of between 0.20 $cm^3.g^{-1}$ and 0.40 $cm^3.g^{-1}$ and preferably between 0.20 $cm^3.g^{-1}$ and 0.35 $cm^3.g^{-1}$ (expressed relative to the anhydride equivalent mass of the zeolite adsorbent).

A zeolite adsorbent that is also preferred in the context of the present invention is one in which the micropore volume evaluated via the t-plot method from the nitrogen ($N_2$) adsorption isotherm at a temperature of 77 K, is between 0.180 $cm^3.g^{-1}$ and 0.290 $cm^3.g^{-1}$, preferably between 0.180 $cm^3.g^{-1}$ and 0.270 $cm^3.g^{-1}$. Said measurement of the micropore volume is calculated after degassing under vacuum ($P<6.7\times10^{-4}$ Pa), at a temperature of between 300° C. and 450° C. for a time ranging from 9 hours to 16 hours, preferably at 400° C. for 10 hours.

In addition, the zeolite adsorbent of the present invention advantageously has a ratio (macropore volume)/(macropore volume+mesopore volume) of between 0.2 and 1, preferably between 0.4 and 0.8 and even more preferably between 0.45 and 0.65.

In the context of the present invention, the mechanical strength is measured via the Shell method series SMS1471-74 adapted for agglomerates less than 1.6 mm in size. This mechanical strength, measured for the zeolite adsorbent defined previously, is generally between 1 MPa and 4 MPa, preferably between 1.5 MPa and 4 MPa, more preferably between 1.8 MPa and 4 MPa and entirely preferably between 2 MPa and 4 MPa.

Another subject of the invention relates to the process for preparing the zeolite adsorbent as defined previously, said process comprising at least the steps of:

a) agglomeration of crystals of at least one zeolite of FAU type with hierarchical porosity, having an outer surface area of between 40 $m^2.g^{-1}$ and 400 $m^2.g^{-1}$, preferably between 40 $m^2.g^{-1}$ and 200 $m^2.g^{-1}$ and more preferably between 40 $m^2.g^{-1}$ and 150 $m^2.g^{-1}$ with a binder comprising at least 80% of clay or of a mixture of clays, which are optionally zeolitizable, and optionally up to 5% of additives and also with an amount of water which allows forming of the agglomerated material; drying of the agglomerates at a temperature of between 50° C. and 150° C.; calcination of the dried agglomerates under a stream of oxidizing and/or inert gas, especially with gases such as oxygen, nitrogen, air, a dry and/or decarbonated air, an oxygen-depleted air, which is optionally dry and/or decarbonated, at a temperature above 150° C., typically between 180° C. and 800° C., preferentially between 200° C. and 650° C., for a few hours, for example from 2 to 6 hours;

b) optionally zeolitization of all or part of the binder by placing the agglomerates obtained in step a) in contact with an alkaline basic solution;

c) cation exchange(s) of the agglomerates from step a) and/or from step b) by placing in contact with a solution of barium ions and/or of potassium ions;

d) optional additional cation exchange of the agglomerates from step c) by placing in contact with a solution of potassium ions;

e) washing and drying of the agglomerates obtained in steps c) or d), at a temperature of between 50° C. and 150° C.; and f) production of the zeolite adsorbent according to the invention by activation of the agglomerates obtained in step e) under a stream of oxidizing and/or inert gas, especially with gases such as oxygen, nitrogen, air, a dry and/or decarbonate air, an oxygen-depleted air, which is optionally dry and/or decarbonated, at a temperature between 100° C. and 400° C., preferably between 200° C. and 300° C. for a time determined as a function of the desired water content and loss on ignition, typically from 1 to 6 hours.

According to a preferred embodiment, said at least one zeolite FAU has an Si/Al atomic ratio preferably between 1.00 and 1.50, preferably between 1.05 and 1.40 and even more preferably between 1.10 and 1.40. As indicated previously, the outer surface area of the crystals used in step a) of the process described above is calculated via the t-plot method from the nitrogen adsorption isotherm at a temperature of 77 K, after degassing under vacuum (P<6.7×10$^4$ Pa), at a temperature between 300° C. and 450° C. for a time ranging from 9 hours to 16 hours, preferably at 400° C. for 10 hours.

Preferably, the zeolite FAU crystals of the adsorbent of the present invention, advantageously used in step a) of the process defined previously, have a number-average diameter of between 0.1 μm and 20 μm, preferably between 0.5 μm and 20 μm, more preferably between 0.5 μm and 10 μm, preferably between 0.5 μm and 5 μm.

The zeolite FAU crystals with a large outer surface area used in step a) may be obtained according to various methods known to those skilled in the art, for example according to the synthesis described by Inayat et al. in *Angew. Chem. Int. Ed.*, 51, (2012), 1962-1965.

It is also possible to prepare said crystals by synthesis by seeding and/or by adjusting the synthetic operating conditions such as the $SiO_2/Al_2O_3$ ratio, the sodium content and the alkalinity of the synthetic mixture or alternatively according to conventional processes for post-treatment of zeolite FAU crystals.

The post-treatment processes generally consist in removing atoms from the already-formed zeolite network, either by one or more acid treatments which dealuminate the solid, these treatments being followed by one or more washes with sodium hydroxide so as to remove the aluminium-based residues formed, as described, for example, by D. Verboekend et al. (*Adv. Funct. Mater.*, 22, (2012), pp. 916-928), or alternatively by treatments which combine the action of an acid and that of a structuring agent which improve the efficacy of the acid treatment, as described, for example, in patent application WO 2013/106 816.

The processes for the direct synthesis of these zeolites (i.e. synthetic processes other than the post-treatment) generally involve one or more structuring agents or sacrificial templates.

The sacrificial templates that may be used may be of any type known to those skilled in the art and especially those described in patent application WO 2007/043 731. According to a preferred embodiment, the sacrificial template is advantageously chosen from organosilanes and more preferentially from [3-(trimethoxysilyl)propyl]octadecyldimethylammonium chloride, [3-(trimethoxy-silyl)propyl]hexadecyldimethylammonium chloride, [3-(trimethoxysilyl)propyl]dodecyl-dimethylammonium chloride, [3-(trimethoxysilyl)propyl]octylammonium chloride, N-[3-(trimethoxysilyl)propyl]aniline, 3-[2-(2-aminoethylamino)ethylamino]propyltrimethoxy-silane, N-[3-(trimethoxysilyl)propyl]-N'-(4-vinylbenzypethylenediamine, triethoxy-3-(2-imidazolin-1-yl)propylsilane, 1-[3-(trimethoxysilyl)propyl] urea, N-[3-(trimethoxy-silyl)propyl]ethylenediamine, [3-(diethylamino)propyl]trimethoxysilane, (3-glycidyloxypropyl)trimethoxysilane, 3-(trimethoxysilyl)propyl methacrylate, [2-(cyclohexenyl)ethyl]-triethoxysilane, dodecyltriethoxysilane, hexadecyltrimethoxysilane, (3-aminopropyl)tri-methoxysilane, (3-mercaptopropyl)trimethoxysilane, (3-chloropropyl)trimethoxysilane, and also mixtures of two or more thereof in all proportions.

Among the sacrificial templates listed above, [3-(trimethoxysilyl)propyl]octadecyldimethylammonium chloride or TPOAC is most particularly preferred.

Use may also be made of sacrificial templates of higher molar mass, for example PPDAs (polydiallyldimethylammonium polymers), PVB (polyvinyl butyral) and other oligomeric compounds known in the field for increasing the diameter of mesopores.

According to a preferred embodiment of the process of the present invention, agglomeration of crystals of at least one zeolite FAU with hierarchical porosity, as described previously, prepared in the presence of a sacrificial template intended to removed, is performed in step a).

This removal may be performed according to the methods known to those skilled in the art, for example by calcinations, and, in a non-limiting manner, the calcinations of zeolite crystals comprising the sacrificial template may be performed under a stream of oxidizing and/or inert gas, especially with gases such as oxygen, nitrogen, air, a dry and/or decarbonated air, an oxygen-depleted air, which is optionally dry and/or decarbonated, at one or more temperatures above 150° C., typically between 180° C. and 800° C., preferentially between 200° C. and 650° C., for a few hours, for example between 2 and 6 hours. The nature of the gases, the temperature increase ramps and the successive temperature stages and their durations will be adapated as a function of the nature of the sacrificial template.

The additional step of removal of the optional sacrificial template may be performed at any moment during the process for preparing the agglomerated zeolite material of the invention. The removal of said sacrificial template may thus advantageously be performed by calcinations of the zeolite crystals before the agglomeration step a), or alternatively concomitantly with the calcinations of the agglomerates during step a).

It would not constitute a departure from the context of the invention if the agglomeration of step a) comprised the agglomeration of several zeolites with hierarchical porosity obtained according to different modes.

The synthesis of FAU type zeolite is generally performed in sodium medium (Na cation). The zeolite FAU crystals thus obtained predominantly, or even exclusively, comprise sodium cations. However, it would not constitute a departure from the context of the invention to use crystals that have undergone one or more cationic exchanges, between the system in Na form, before or after the optional removal of the sacrificial template if this step is performed before performing step a) and its implementation in step a). In this case, step c) and optionally the exchange step d) consequently become unnecessary.

The size of the zeolite FAU crystals used in step a) and of the zeolite FAU crystals in the agglomerates according to the invention is measured by observation with a scanning electron microscope (SEM). As indicated previously, preferably, the mean diameter of the elements is between 0.1 μm and 20 μm. This SEM observation also makes it possible to confirm the presence of non-zeolite phase comprising, for example, residual binder (not converted during the zeolitization step) or any other amorphous phase in the agglomerates.

In the present document, the term "number-average diameter" or "size" is used especially for the zeolite crystals. The method for measuring these magnitudes is explained later in the description.

The agglomeration and forming (step a) may be performed according to any technique known to those skilled in the art, such as extrusion, compacting, agglomeration on a granulating place, granulating drum, atomization and the like, and preferably by agglomeration on a granulating plate, granulating drum, atomization and the like.

The proportions of agglomeration binder (see the definition later) and of zeolite used are typically those of the prior art, i.e. from 1% to 50% by weight, relative to the total weight (binder+zeolite). The agglomerates derived from step a), whether in the form of beads, extrudates or the like, preferably have a volume-average diameter of between 0.2 mm and 0.6 mm, preferably between 0.3 mm and 0.6 mm.

After step a), the finest agglomerates may be removed by cycloning and/or screening and/or the excessively coarse agglomerates being removed by screening or crushing, in the case of extrudates, for example.

The binder included in the zeolitic agglomerated material of the present invention comprises, and preferably consists of, a clay or a mixture of clays. These clays are preferably chosen from kaolins, kaolinites, nacrites, dickites, halloysites, attapulgites, sepiolites, montmorillonites, bentonites, illites and metakaolins, and also mixtures of two or more thereof in all proportions.

In the case of the optional zeolitization step b), the agglomeration binder used in step a) contains at least 80%, preferably at least 90%, more preferabkly at least 95%, more particularly at least 96% by weight of at least one zeolitizable clay and may also contain other mineral binders such as bentonite, attapulgite and the like. The term "zeolitizable clay" means a clay or a mixture of clays that can be converted into zeolitic material, usually via the action of an alkaline basic solution. The zeolitizable clay generally belongs to the family of kaolins, kaolinites, nacrites, dickites, halloysite and/or metakaolins. Kaolin is preferred and most commonly used.

Among the additives optionally used in step a) may be a source of silica known to a person skilled in the art, who is a specialist in zeolite synthesis, for example colloidal silica, diatomaceous earths, perlite, calcination ash (fly ash), sand, or any other form of solid silica.

During step a), besides the zeolite FAU crystals and the binder, other additives may also be added, for example additives for facilitating the agglomeration or for improving the hardening of the agglomerates formed, such as lignin, starch, carboxymethylcellulose and other additives known to those skilled in the art.

For the calcination included in step a), the nature of the gases, the temperature increase ramps and the successive temperature stages, and also the respective durations thereof, will be adapted as a function of the nature of the sacrificial template to be removed and as a function of the nature of the binder used in the agglomeration step a).

In particular, if the agglomeration binder contains one or more zeolitizable clays, the calcination makes it possible to convert the zeolitizable clay, typically kaolin, into metakaolin, which may be converted thereafter into zeolite during the zeolitization step (step b)). This principle is outlined in *Zeolite Molecular Sieves* by D. W. Breck, John Wiley and Sons, New York, (1973), p. 314-315.

The zeolitization of the agglomeration binder is performed according to any method that is now well known to those skilled in the art, and may be performed, for example, by immersing the product obtained from step a) in an alkaline and generally aqueous basic solution, for example an aqueous sodium hydroxide and/or potassium hydroxide solution.

As a general rule, the concentration of the alkaline zeolitization solution is preferably between 0.5 M and 5 M. The zeolitization is preferably performed hot, at a temperature above room temperature, and typically at temperatures from about 80° C. to 100° C., for example between room temperature (i.e. about 20° C.) and the boiling point of the alkaline zeolitization solution. The duration of the zeolitization process is generally between a few tens of minutes and a few hours, preferably between about 1 hour and 8 hours.

The cation-exchange steps c) and d) are performed according to the standard methods known to those skilled in the art, and usually by placing the agglomerates obtained from step a) in contact with a barium and/or potassium salt, such as barium chloride ($BaCl_2$) and/or potassium chloride (KCl), in aqueous solution at a temperature between room temperature and 100° C., and preferably between 80° C. and 100° C., so as rapidly to obtain high barium oxide contents, i.e. preferably greater than 10%, preferably greater than 15%, very preferably greater than 20%, even more preferably greater than 23%, or even greater than 33% by weight relative to the total mass of the adsorbent.

Advantageously, the content of barium (expressed as barium oxide BaO) is between 23% and 42% and typically between 30% and 40% by weight relative to the total weight of the adsorbent. It is preferred to work with a large excess of barium ions relative to the cations of the zeolite that it is desired to exchange, typically an excess of the order of 10 to 12, advantageously by performing successive exchanges.

The optional potassium exchange (step d) may be performed before and/or after the barium exchange (step c). As indicated previously, it is also possible to agglomerate in step a) zeolite FAU crystals already containing barium or potassium or barium and potassium ions (pre-exchange of the cations present in the starting FAU-type zeolite, typically sodium cations, with barium or potassium or barium and potassium ions before step a) and to dispense with steps c) and/or d) (or not).

Surprisingly, the Applicant has observed that the cation-exchange step, which may be difficult due to the relative fragility of the structure of the zeolite crystals, does not affect the intrinsic outer surface area and micropore volume properties (relative to the mass of the adsorbent once exchanged) of said zeolite crystals.

After the cation-exchange step(s), washing is then generally performed, preferably with water, followed by drying of the agglomerate thus obtained.

The activation which follows the drying is performed conventionally, according to the methods known to those skilled in the art, for example at a temperature generally between 100° C. and 400° C., preferably between 200° C. and 300° C. for a time determined as a function of the desired water content and loss on ignition, typically from 1 to 6 hours.

The zeolite adsorbent described above has properties that are entirely suited and advantageous for applications in which molecular sieves are commonly used, and especially in separation processes, and most particularly industrial processes for separating isomers.

Thus, and according to a third aspect, the present invention relates to the use of at least one zeolite adsorbent according to the invention and as has just been defined, for the separation of para-xylene from aromatic fractions containing 8 carbon atoms.

The use according to the present invention which involves a zeolite adsorbent comprising at least zeolite of Ba(K)XPH type (for zeolite X with hierarchical porosity, exchanged with barium or with barium and potassium) makes it possible to propose a process for separating para-xylene from a mixture of C8 aromatic hydrocarbons whose production efficiency is further improved relative to the prior art.

Thus, and according to yet another aspect, the present invention relates to a process for separating para-xylene from a mixture of C8 aromatic hydrocarbons, using at least one zeolite adsorbent as has just been defined.

It has been discovered, entirely surprisingly, that the process of the invention using at least one zeolite adsorbent comprising at least one zeolite Ba(K)XPH makes it possible to obtain a production efficiency towards para-xylene that is further improved relative to the prior art.

More specifically, the present invention relates to a process for separating para-xylene from a mixture of C8 aromatic hydrocarbons, whose production efficiency is improved, the improvement being obtained by using the zeolite adsorbent defined previously and which comprises zeolite X with hierarchical porosity and in which the compensating ions are predominantly barium or barium and potassium, said adsorbents having particular size and morphology characteristics relative to a conventional adsorbent.

More particularly, the invention relates to a process for separating para-xylene from aromatic $C_8$ isomer fractions, which consists in using as para-xylene adsorption agent a zeolite adsorbent as defined previously, said process being performed in liquid-phase but also gas-phase processes.

In a preferred embodiment, the invention relates to a process for producing high-purity para-xylene from an aromatic hydrocarbon feedstock containing isomers containing 8 carbon atoms, comprising at least the following steps:
 a) placing the feedstock in contact, under suitable adsorption conditions, with a bed of zeolite adsorbent as defined previously, so as preferentially to adsorb the para-xylene,
 b) placing the adsorbent bed in contact, under desorption conditions, with a desorbent, which is preferentially either toluene or para-diethylbenzene,
 c) removing from the adsorbent bed a stream containing the desorbent and the products of the feedstock that are the least selectively adsorbed,
 d) removing from the adsorbent bed a stream containing the desorbent and the para-xylene,
 e) separation of the stream obtained from step c) into a first stream containing the desorbent and a second stream containing the products of the feedstock that are the least selectively adsorbed, and
 f) separation of the stream obtained from step d) into a first stream containing the desorbent and a second stream containing para-xylene at a level of purity greater than or equal to 75% and preferably greater than or equal to 99.7%, and preferably at least 99.8%.

The process may also optionally include the following steps:
 g) a crystallization step in a crystallizer consisting of the crystallization of the para-xylene obtained from step f), making it possible to obtain, firstly, crystals of para-xylene soaked with their mother liquor, and, secondly, a mother liquor which may be partly, or even totally, recycled as a mixture with the fresh feedstock at the inlet of the simulated moving bed adsorption unit, and
 h) a step of washing the crystals obtained from step g) after which para-xylene is recovered in a purity of at least 99.7% and preferably of at least 99.8%.

The desired product may thus be separated out by preparative adsorption liquid chromatography (batchwise), advantageously in a simulated moving bed, i.e. with simulated counter-current or simulated co-current, and more particularly with simulated counter-current.

Simulated moving bed chromatographic separation with simulated counter-current is well known in the prior art. As a general rule, a simulated moving bed separation unit comprises at least one adsorption column containing a plurality of beds of an adsorbent, interconnected in a closed loop. The simulated moving bed separation unit comprises at least three chromatographic zones, and optionally four or five, each of these zones consisting of at least one bed or a column portion and included between two successive feed or withdrawal points.

Typically, at least one feedstock to be fractionated and a desorbent (occasionally known as an eluent) are fed in and at least one raffinate and an extract are removed. The feed points and withdrawal points are modified over time, typically shifted towards the bottom of a bed, in a synchronous manner, or optionally an asynchronous manner during a fractionation of "Varicol" type.

By definition, each of the operating zones is referred to by a number:
 Zone 1=zone of desorption of the desired product (contained in the extract) between the injection of the desorbent and the removal of the extract;
 Zone 2=zone of desorption of the compounds of the raffinate, between the removal of the extract and the injection of the feedstock to be fractionated;
 Zone 3=zone of adsorption of the desired product, between the injection of the feedstock and the removal of the raffinate; and
 Zone 4between the removal of raffinate and the injection of the desorbent.

The operating conditions of an industrial, adsorption unit of simulated counter-current type are in general as follows:
 number of beds: 4 to 24;
 number of zones: at least 4;
 temperature: 100 to 250° C., preferably 150 to 190° C.;
 pressure between the bubble pressure of xylenes at the process temperature and 3 MPa;
 ratio of the flow rates of desorbent to feedstock: 0.7 to 2.5 (for example 0.9 to 1.8 for a stand-alone adsorption unit and 0.7 to 1.4 for an adsorption unit combined with a crystallization unit);
 degree of recycling: 2 to 12, preferably 2.5 to 5.
 cycle time, corresponding to the time between two injections of desorbent on a given bed: advantageously between 4 and 18 minutes.

Reference may also be made to the teaching of patents U.S. Pat. Nos. 2,985,589, 5,284,992 and 5,629,467.

The operating conditions of an industrial simulated co-current adsorption unit are generally the same as those functioning with simulated counter-current except for the degree of recycling, which is generally between 0.8 and 7. Reference may be made to patents U.S. Pat. Nos. 4,402,832 and 4,498,991.

The desorption solvent may be a desorbent whose boiling point is less than that of the feedstock, such as toluene, but also a desorbent whose boiling point is greater than that of the feedstock, such as para-diethylbenzene (PDEB). The selectivity of the adsorbents according to the invention for the adsorption of the para-xylene contained in $C_8$ aromatic fractions is optimal when their loss on ignition measured at 900° C. is generally between 4.0% and 8.0% and preferably between 4.7% and 6.7%. Water and a small amount of carbon dioxide are included in the loss on ignition.

The water content in the hydrocarbon-based effluents is preferentially adjusted to between 20 ppm and 150 ppm for a process temperature from 165° C. to 185° C., by adding water to the feedstock comprising the aromatic hydrocarbon isomer fractions containing 8 carbon atoms and/or to the desorbent, so as to obtain optimum production efficiency results.

More precisely, the object of the invention is to optimize the solid adsorbent used in the process for separating para-xylene by simulated moving bed adsorption, to maximize the performance of this process. In general, the performance desired for the separation of a feedstock containing xylenes are a maximum production efficiency for a purity of the desired product in the extract streams at least equal to 99.7% and even 99.8%, or even 99.9%, and an overall yield of desired product at least equal to 90%, or even greater than 95% and preferably greater than 97%, or even greater than 98%.

The present invention is now described with the aid of the examples that follow, the purpose of which is to illustrate certain embodiments of the invention, without, however, limiting the scope of the said invention, as is claimed in the attached claims.

Characterization Techniques

Particle Size of the Zeolite Crystals—Detection of the Mesopores

The estimation of the number-average diameter of the zeolite FAU crystals contained in the zeolite adsorbents according to the invention is performed by observation with a scanning electron microscope (SEM).

In order to estimate the size of the zeolite crystals in the adsorbents, a set of images is taken at a magnification of at least 5000. The diameter of at least 200 crystals is then measured using dedicated software. The accuracy is of the order of 3%.

Figure 1:
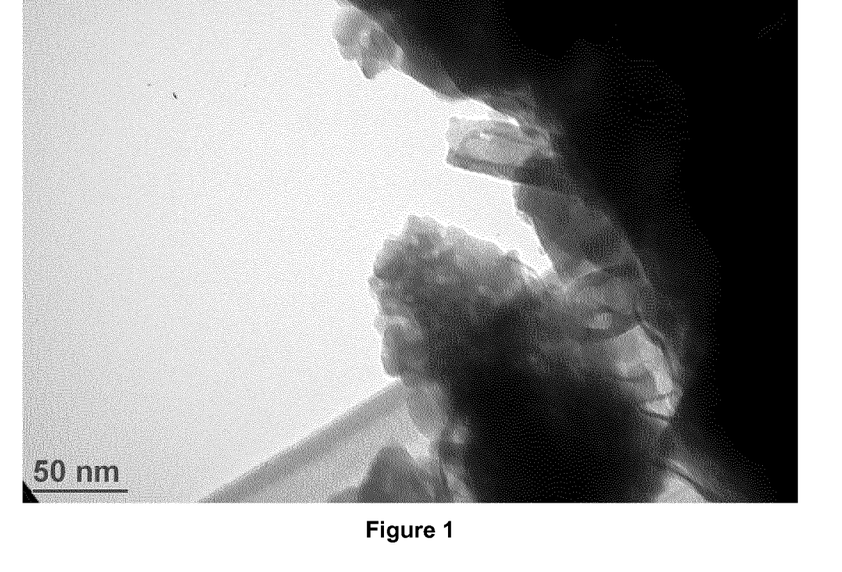
FIG. 1: TEM images, in which mesoporosity is clearly visible.
Figure 2:
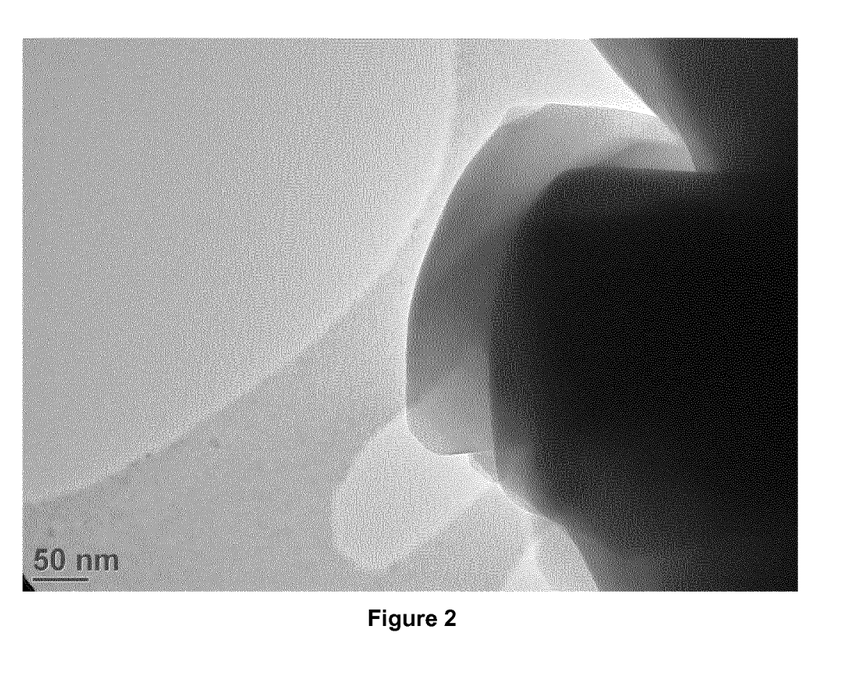
FIG. 2: Filled crystals.

As indicated in U.S. Pat. No. 7,785,563, TEM also makes it possible to check whether the zeolite crystals contained in the adsorbent are filled zeolite crystals (i.e. non-mesoporous) or aggregates of filled zeolite crystals or mesoporous crystals (cf. the comparison of the TEM images in FIG. 1, in which the mesoporosity is clearly visible, and FIG. 2 which show filled crystals). TEM observation thus makes it possible to visualize the presence or absence of the mesopores. Preferably, the adsorbents of the process according to the invention very predominantly contain, i.e. typically more than 80% and preferably more than 90% by number, mesoporous zeolite crystals rather than filled crystals. This statistical analysis is advantageously performed by analysing at least 50 TEM or SEM images (SEM on sections of samples obtained by ionic polishing).

Chemical Analysis of the Zeolite Adsorbent—Si/Al Ratio and Degree of Exchange

An elemental chemical analysis of the zeolite adsorbent may be performed according to various analytical techniques known to those skilled in the art. Among these techniques, mention may be made of the technique of X-ray fluorescence chemical analysis as described in standard NF EN ISO 12677: 2011 on a wavelength dispersive spectrometer (WDXRF), for example the Tiger S8 machine from the company Bruker.

X-ray fluorescence is a non-destructive spectral technique exploiting the photoluminescence of atoms in the X-ray range, to establish the elemental composition of a sample. Excitation of the atoms, generally with a beam of X-rays or by bombardment with electrons, generates specific radiations after returning to the ground state of the atom. The X-ray fluorescence spectrum has the advantage of depending very little on the chemical combination of the element, which offers a precise determination, both quantitatively and qualitatively. A measuring uncertainty of less than 0.4% by weight is conventionally obtained after calibration for each oxide, typically BaO, $Na_2O$ and $K_2O$.

These elemental chemical analyses make it possible both to check the Si/Al atomic ratio of the zeolitic adsorbent and of the zeolite used during the preparation of said adsorbent, and to check the quality of the ion exchange. In the description of the present invention, the measuring uncertainty of the Si/Al atomic ratio is ±5%.

The quality of the ion exchange is linked to the number of moles of sodium oxide, $Na_2O$, remaining in the zeolite agglomerate after exchange. More specifically, the degree of exchange with barium ions is estimated by evaluating the ratio between the number of moles of barium oxide, BaO, and the number of moles of the combination (BaO+$Na_2O$). Similarly, the degree of exchange with barium and/or potassium ions is estimated by evaluating the ratio between the number of moles of the combination barium oxide+potassium oxide (BaO+$K_2O$) and the number of moles of the combination (BaO+$K_2O$+$Na_2O$). It should be noted that the contents of various oxides are given as weight percentages relative to the total weight of the anhydrous zeolite adsorbent.

Mass Amount of the Zeolite Fractions of the Zeolite Adsorbents

The mass amount of the zeolite fractions (content of crystalline phase) is measured by X-ray diffraction analysis, known to those skilled in the art by the abbreviation XRD. This analysis is performed on a Bruker brand machine, and the amount of zeolite fractions is then evaluated from the peak intensities of the diffractograms taking as reference the peak intensities of a suitable reference (zeolite of the same chemical nature assumed to be 100% crystalline under cationic treatment conditions identical to those of the adsorbent under consideration). The peaks which make it possible to access the content of crystalline phase are the most intense peaks of the angular 2 θ zone between 9° and 37°, namely the peaks observed in the angular 2 θ ranges between, respectively, 11° and 13°, between 22° and 26° and between 31° and 33°.

Particle Size of the Zeolite Adsorbents

The determination of the volume-average diameter of the zeolite adsorbents of the process according to the invention is performed by analysis of the particle size distribution of a sample of adsorbent by imaging according to standard ISO 13322-2:2006, using a conveyor belt which allows the sample to pass before the objective lens of the camera.

The volume-average diameter is then calculated from the particle size distribution by applying standard ISO 9276-2: 2001. In the present document, the name "volume-average diameter" or "size" is used for the zeolite adsorbents. The precision is of the order of 0.01 mm for the range of sizes of the adsorbents that are useful in the context of the present invention.

Shape Factor of the Zeolite Adsorbents

Scanning electron microscopy allows an observation and a visual assessment of the morphology of the zeolite adsorbents. Morphometry, based on video acquisition and on image analysis, gives access to quantifiable parameters characteristic of the morphology of the particles. Various commercial devices exist: by way of example, mention may be made of the machines Morphologi G2 from Malvern, Camsizer from Retsch, Alpaga 500 Nano from Occhio, described on the Internet pages www.malvern.com, www.retsch-technology.com, or encore www.occhio.be.

Using the Alpaga 500 Nano machine, acquisitions are taken on 10 000 particles for each sample tested and the elongation and roundness parameters are calculated for each particle.

The mathematical tools used for their calculation are developed in E. Pirard's doctoral thesis (1993, University of Liège, 253 pages) entitled *Euclidian morphometry of flat figures. Applications to the analysis of granular materials*. The document entitled *The descriptive and quantitative representation of particle shape and morphology* is available under the reference ISO/DIS 9276-6.

The sphericity is evaluated using the following two parameters, as described, for example, in patent application WO 2008/152 319:

- the roundness is expressed in percentages, and is calculated from the distribution moments of the circles inscribed in the particle that are tangent to the contour points of the particle, via complex filtering; it is representative of the variation in the radius of curvature of the particles and reflects the maturity of a grain in an abrasion process. The gentle asperities are more significant than the very protruding asperities. The more the shape of the particles approaches perfect sphericity, the closer the roundness is to 100%;
- the elongation, expressed as a percentage, is occasionally referred to in the literature as the "elliptical shape factor" and is calculated from the ratio between the large and the small axis of the inertial ellipsis of the particle, a and b, according to the formula $A=100(1-a/b)$. The elongation is equal to 0 for a spherical article, it increases for shapes departing from sphericity and tends toward 100 for an elongated particle such as fibre.

Mechanical Strength of the Zeolite Adsorbents

The crush strength of a bed of zeolite adsorbents as described in the present invention is characterized according to the Shell method series SMS1471-74 (Shell Method Series SMS1471-74 *Determination of Bulk Crushing Strength of Catalysts. Compression-Sieve Method*), associated with the BCS Tester machine sold by the company Vinci Technologies. This method, initially intended for the characterization of catalysts from 3 mm to 6 mm, is based on the use of a 425 µm screen, which makes it possible especially to separate the fines created during the crushing. The use of a 425 µm screen remains suited to zeolite adsorbents with a diameter of greater than 1.6 mm, but should be adapted according to the particle size of the adsorbents that it is desired to characterize.

The adsorbents used in the process according to the present invention, preferably in the form of beads, have a volume-average diameter of between 0.2 mm and 0.6 mm and in particular between 0.3 mm and 0.6 mm. Consequently, a 100 µm screen is used instead of the 425 µm screen mentioned in the Shell method standard SMS1471-74.

The measuring protocol is as follows: a sample of 20 cm³ of zeolite adsorbents, screened beforehand with the appropriate screen (100 µm) and dried beforehand in an oven for at least 2 hours at 250° C. (instead of 300° C. mentioned in Shell method standard SMS1471-74), is placed in a metal cylinder of known internal cross section. An increasing force is imposed in stages on this sample by means of a piston, through a bed of 5 cm³ of steel balls so as better to distribute the force exerted by the piston on the adsorbent agglomerates (use of balls 2 mm in diameter for particles of spherical shape with a diameter strictly less than 1.6 mm). The fines obtained at the various pressure stages are separated out by screening (appropriate 100 µm screen) and weighed.

The bulk crushing strength is determined by the pressure in megaPascals (MPa) for which the cumulative amount of fines passing through the screen is 0.5% by weight of the sample. This value is obtained by plotting on a graph the mass of fines obtained as a function of the force applied to the adsorbent bed and by interpolating to 0.5% by mass of cumulative fines. The mechanical bulk crushing strength is typically between a few hundred kPa and a few tens of MPa and generally between 0.3 MPa and 3.2 MPa. The precision is conventionally less than 0.1 MPa.

Micropore Volume, Outer Surface Area and Diameter of the Mesopores

The crystallinity of the adsorbents is also evaluated by measuring their micropore volume and comparing it with that of a suitable reference (adsorbent with an identical binder content, with 100% crystalline zeolite under identical cationic treatment conditions or theoretical zeolite). This micropore volume is determined from the measurement of the adsorption isotherm of the gas, such as nitrogen, at its liquefaction temperature.

Prior to the adsorption, the zeolite adsorbent is degassed at between 300° C. and 450° C. for a time of between 9 hours and 16 hours under vacuum ($P<6.7\times10^{-4}$ Pa). Measurement of the nitrogen adsorption isotherm at 77 K is then performed on an ASAP 2020 M machine from Micromeritics, taking at least 35 measurement points at relative pressures with a ratio $P/P_0$ of between 0.002 and 1.

The micropore volume and the outer surface area are determined from the isotherm obtained, via the t-plot method by applying standard ISO 15901-3:2007 and calculating the statistical thickness t via the Harkins-Jura equation. The micropore volume and the outer surface area are obtained by linear regression on the points of the t-plot between 0.45 and 0.57 nm, respectively from the y-axis to the origin and from the slope of the linear progression. The evaluated micropore value is expressed in cm³ of liquid adsorbate per gram of anhydrous adsorbent. The outer surface area is expressed in m² per gram of anhydrous adsorbent.

Interpenetration of the nitrogen adsorption isotherm at 77 K via the Barrett-Joyner-Halenda method (BJH method, proposed in 1951) also makes it possible to obtain the pore size distribution, and especially the mesopore distribution. The mesopore size distribution by volume is represented by the curve dV/d(d) as a function of the mean pore diameter.

Macropore and Mesopore Volume and Grain Density

The macropore and mesopore volumes are measured by mercury intrusion porosimetry. An Autopore® 9500 mercury porosimeter from Micromeritics is used to analyse the distribution of the pore volume contained in the macropores and in the mesopores.

The experimental method, described in the operating manual for the machine which refers to standard ASTM D4284-83, consists in placing a sample of adsorbent (zeolitic granular material to be measured) (known loss on ignition) weighed beforehand, in a porosimeter cell, and then, after first degassing (vacuum pressure of 30 µmHg for at least 10 minutes), in filling the cell with mercury at a given pressure (0.0036 MPa) and then in applying a pressure increasing in stages up to 400 MPa so as to make the mercury gradually penetrate into the pore network of the sample.

The relationship between the applied pressure and the apparent pore diameter is established by assuming cylindrical pores, a contact angle between the mercury and the pore wall of 140° and a mercury surface tension of 485 dynes/cm. The cumulative amount of mercury introduced as a function of the applied pressure is recorded. The value at and above which the mercury fills all the inter-granular voids is set at 0.2 MPa, and it is considered that beyond this value, the mercury penetrates into the pores of the granular material. The grain volume (Vg) is then calculated by subtracting the cumulative volume of mercury at this pressure (0.2 MPa) from the volume of the porosimeter cell, and by dividing this difference by the mass of the anhydrous equivalent granular material, i.e. the mass of said material corrected for the loss on ignition. The grain density is the inverse of the grain volume (Vg), and is expressed in grams of anhydrous adsorbent per cm$^3$.

The macropore volume of the granular material is defined as being the cumulative volume of mercury introduced at a pressure of between 0.2 MPa and 30 MPa, corresponding to the volume contained in the pores with an apparent diameter of greater than 50 nm. The mesopore volume of the granular material is defined as being the cumulative volume of mercury introduced at a pressure of between 30 MPa and 400 MPa.

In the present document, the macropore and mesopore volumes of the zeolite adsorbents, expressed in cm$^3$.g$^{-1}$, are thus measured by mercury intrusion and related to the mass of the sample as anhydrous equivalent, i.e. the mass of said material corrected for the loss on ignition.

Loss on Ignition of the Zeolite Adsorbents

The loss on ignition is determined under an oxidizing atmosphere, by calcination of the sample in air at a temperature of 950° C.±25° C., as described in standard NF EN 196-2 (April 2006). The measurement standard deviation is less than 0.1%.

EXAMPLE A

Preparation of Paste from XPH Crystals

A homogeneous mixture consisting of 1600 g anhydrous equivalent of mesoporous zeolite X crystals synthesized according to the procedure of Inayat et al. (*Angew. Chem. Int. Ed.,* 51, (2012), 1962-1965), 350 g anhydrous equivalent of kaolin, 130 g of colloidal silica sold under the trade name Klebosol® 30 (containing 30% by weight of SiO$_2$ and 0.5% of Na$_2$O) and the amount of water that allows extrusion of the mixture. The loss on ignition of the paste before forming is 44%.

EXAMPLE B

Preparation of Paste from X Crystals of Diameter 1.6 μm

A homogeneous mixture consisting of 1600 g anhydrous equivalent of zeolite X crystals synthesized according to the procedure described in procedure B of patent application WO 2008/009 845), 300 g anhydrous equivalent of kaolin, 130 g of colloidal silica sold under the trade name Klebosol® 30 (containing 30% by weight of SiO$_2$ and 0.5% of Na$_2$O) and the amount of water which allows extrusion of the mixture, is prepared.

EXAMPLE C

Preparation of Agglomerated Adsorbents by Extrusion/Crushing/Screening

Starting with the paste prepared according to procedure A or B above, extrudates 1.6 mm in diameter are formed. The extrudates are dried overnight in a ventilated oven at 80° C. They are then calcined for 2 hours at 550° C. under a stream of nitrogen, and then for 2 hours at 550° C. under a stream of decarbonated dry air and then crushed so as to recover grains by screening at the desired particle size, namely: crushed material with a particle size of 0.4 mm (obtained by selection of the crushed material with an equivalent diameter of between 0.3 and 0.5 mm so that the volume-average diameter is equal to 0.4 mm).

EXAMPLE D

Preparation of Agglomerated Adsorbents by Granulation/Screening

The paste prepared according to procedure A or B is used on a granulating plate so as to make beads of agglomerated adsorbent. Selection by screening of the beads obtained is performed at the desired particle size, namely:
  beads with a particle size of 0.4 mm: selection of the beads with a diameter of between 0.3 and 0.5 mm so that the volume-average diameter is equal to 0.4 mm;
  beads with a particle size of 0.54 mm: selection of the beads with a diameter of between 0.3 and 0.8 mm so that the volume-average diameter is equal to 0.54 mm;
  beads with a particle size of 0.7 mm: selection of the beads with a diameter of between 0.4 and 1.0 mm so that the volume-average diameter is equal to 0.7 mm.

The beads are dried overnight in a ventilated oven at 80° C. They are then calcined for 2 hours at 550° C. under a stream of nitrogen, and then for 2 hours at 550° C. under a stream of decarbonated dry air.

EXAMPLE E

Zeolitization (Optional)

The granules or beads obtained in Examples C or D are placed in a jacketed glass reactor regulated at a temperature of 100° C.±1° C., and 1.5 L of aqueous sodium hydroxide solution of concentration 100 g.L$^{-1}$ are then added and the reaction medium is left stirring for 3 hours. The granules are then washed in 3 successive washing operations with water followed by emptying the reactor. The washing efficacy is ensured by measuring the final pH of the washing waters, which is between 10 and 10.5.

EXAMPLE F

Exchange—Activation

The granules or beads obtained in step C or D or optionally E are exchanged by means of aqueous 0.7 M barium chloride (BaCl$_2$) solution at 95° C. in 4 steps. At each step, the volume ratio of solution/mass of solid is 20 mL.g$^{-1}$ and the exchange is continued for 4 hours at each time. Between each exchange, the solid is washed several times so as to free it of the excess BaCl$_2$. It is then dried at 80° C. for 2 hours and finally activated at a temperature of 250° C. for 2 hours under a stream of nitrogen.

EXAMPLE 1

Comparative Example

An adsorbent in the form of crushed material (i.e. non-spherical elements) with a particle size of 0.4 mm is prepared from the successive steps described in Examples A, C and E. This adsorbent is characterized according to the described techniques.

The degree of overall barium exchange is 97% and the loss on ignition (measured at 900° C.) is 5.5%. The micropore volume and the outer surface area measured according to the t-plot method from the nitrogen adsorption isotherm at 77 K after degassing under vacuum at 400° C. for 10 hours are, respectively, 0.192 cm$^3$.g$^{-1}$ and 70 m$^2$.g$^{-1}$.

The total volume contained in the macropores and the mesopores (sum of the macropore volume and of the mesopore volume) measured by mercury intrusion, is 0.33 cm$^3$.g$^{-1}$. The ratio (macropore volume)/(macropore volume+mesopore volume) is equal to 0.6. The grain density of the adsorbent (calculated by dividing the mass of the anhydrous equivalent sample by the volume of the sample evaluated from the volume of mercury introduced at a pressure of 0.2 MPa) is 1.10 g.cm$^{-3}$ anhydrous equivalent.

The, adsorbent is used to fill a stainless-steel column with an inside diameter of 0.77 cm and 1 m long, equipped at the end with a filtering grate. At least three packings are performed with the adsorbent whose loss on ignition was measured at 5.5% so as to estimate a mean packing density value for the adsorbent: 0.730±0.010 g.cm$^{-3}$ is obtained, which makes it possible to evaluate the bed porosity, i.e. the proportion of void between the grains of adsorbent relative to the column volume, as 37.3±0.8%. The roundness of the adsorbent in crushed form is 57%, and the elongation is 9%.

EXAMPLE 2

According to the Invention

An absorbent is prepared in the form of beads with a particle size of 0.4 mm from the successive steps described in Examples A, D and E. The adsorbent thus prepared is characterized according to the described techniques.

The degree of overall barium exchange is 96.4% and the loss on ignition (measured at 900° C.) is 5.40%. The micropore volume and the outer surface area measured according to the t-plot method from the nitrogen adsorption isotherm at 77 K after degassing under vacuum at 400° C. for 10 hours are, respectively, 0.195 cm$^3$.g$^{-1}$ and 63 m2$_g^{-1}$.

The total volume contained in the macropores and the mesopores (sum of the macropore volume and of the mesopore volume) measured by mercury intrusion, is 0.31 cm$^3$.e. The ratio (macropore volume)/(macropore volume+mesopore volume) is equal to 0.65. The grain density of the adsorbent (calculated by dividing the mass of the anhydrous equivalent sample by the volume of the sample evaluated from the volume of mercury introduced at a pressure of 0.2 MPa) is 1.14 g.cm$^{-3}$ anhydrous equivalent.

The adsorbent thus prepared is used to fill a stainless-steel column with an inside diameter of 0.77 cm and 1 m long, equipped at the end with a filtering grate. Several packings of the adsorbent whose loss on ignition was measured at 5.4% are performed so as to estimate a mean packing density value for the adsorbent: 0.764±0.008 g.cm$^{-3}$ is obtained, which makes it possible to evaluate the bed porosity, i.e. the proportion of void between the grains of adsorbent relative to the column volume, at 33.0±0.7%.
The roundness of the adsorbent in the form of beads is 77%, and the elongation is 3%.

Comparison of the adsorbents of Example 1 and Example 2 shows that the bed porosity during packing with agglomerates with a roundness of 77%, indicating a morphology close to sphericity, is more than 4% absolute less than the bed porosity obtained during packing with crushed agglomerates with a roundness of 57%. A bed with a lower bed porosity indicates greater compactness of the agglomerates, i.e. a greater amount of adsorbent per bed volume, which will have as a consequence greater production efficiency during the use of these adsorbents in the separation of para-xylene. Specifically, the production efficiency corresponds to the amount of para-xylene produced per unit of time and per bed volume.

EXAMPLE 3

Packing Tests and Xylene Separation Performance

Adsorbents are prepared in the form of beads with a roundness equal to 80%, of different particle sizes: 0.4 mm-0.54 mm (according to the invention) and 0.7 mm (comparative) from the following successive steps:
  steps A, D and F for the adsorbents starting from crystals of type X zeolite FAU with hierarchical porosity (mesoporous zeolite FAU X)
  steps B, D, E and F for the adsorbents starting from X crystals of diameter 1.6 μm.

These various adsorbents are tested to evaluate their performance in the separation of para-xylene on a simulated counter-current chromatography pilot consisting of 12 columns in series 2 cm in diameter. Several column lengths may be used: 0.5 m, 1 m or 2 m. The circulation between the last and the first column is performed by means of a recycling pump. At each intercolumn link, either a feedstock to be separated or desorbent may be injected. Either a raffinate or an extract may also be withdrawn.

The set of columns and feed valves is placed in an oven at 175° C. and the pressure is maintained above 15 bar (1.5 MPa). The shifting of the various injection or withdrawal points is simulated according to a permutation time that may be adjusted. The beds are divided into 4 chromatographic zones according to the following configuration:
  2 beds between the injection of desorbent and the withdrawal of extract
  5 beds between the withdrawal of extract and the injection of feedstock
  3 beds between injection of feedstock and the withdrawal of raffinate
  2 beds between the withdrawal of raffinate and the injection of desorbent.

The feedstock is composed of 21.3% of para-xylene, 19.6% of ortho-xylene, 45.1% of meta-xylene and 14.0% of ethylbenzene. The desorbent used is para-diethylbenzene. The above percentages are expressed as weight percentages.

In a first stage, the test is performed using an adsorbent according to the prior art, noted "A(comp)" hereinbelow. A(comp) is an adsorbent with a particle size of 0.7 mm prepared from zeolite X crystals with a number-average diameter of 1.6 μm, prepared in an identical manner to Example 4 of patent WO 2008/009 845, except for the forming step, which is performed by granulation so as to obtain spherical beads (step D) rather than crushed material, which makes it possible to optimize the packing of the column via a bed porosity that is smaller by virtue of the sphericity of the agglomerates (roundness of 80%). This test makes it possible to determine the injection rates of feedstock and of desorbent required to obtain para-xylene in a purity of 99.7% and a yield of at least 98%.

By using columns 2 m long and packed with the reference adsorbent, para-xylene is obtained as the extract in a yield of 98.5% by injecting the feedstock at a rate of 40.8 g.min$^{-1}$ and the desorbent at a rate of 48.7 g.min$^{-1}$. The pressure difference measured between the first and the last column is 3.5 bar (0.35 MPa).

Thereafter, all of the adsorbents are tested by applying the same injection rates, i.e. the rates of feedstock and of desorbent, and by regulating the zone flow rates in the adsorber so as to obtain a purity of 99.7%. The yields are reported in Table 1, given that the minimum yield level required is 98%.

The 2 m long columns are first packed with beads of the same particle size as the reference adsorbent, namely 0.7 mm, of an adsorbent prepared with the XPH crystals. By applying the injection rates of feedstock and of desorbent, a yield of 98.5% is achieved. Under these operating conditions, the pressure difference (ΔP) measured between the first and the last column increases relative to the reference case, and rises to 3.7 bar (0.37 MPa). Given this pressure increase, a person skilled in the art would not be inclined to reduce the diameter of adsorbent beads prepared from XPH crystals, given that the linear pressure loss increases with the decrease in particle size of the beads.

However, the, tests using beads with a reduced particle size of adsorbent based on zeolite X crystals with hierarchical porosity (XPH), i.e. an adsorbent according to the invention (noted "A(inv)" in the rest of the present description), show that it is possible to obtain para-xylene (purity of 99.7%) with a yield of at least 98%, by injecting flow rates of feedstock and of desorbent that are identical to the reference case, respectively 40.8 g.min$^{-1}$ and 48.7 g.min$^{-1}$, while at the same time using shorter columns, i.e. using a smaller amount of adsorbent, and doing so without increasing the pressure loss in the unit. The comparative tests performed with the same column lengths and beads of the same particle size of adsorbent prepared with conventional zeolite X crystals 1.6 μm in diameter do not make it possible to obtain para-xylene with the required performance (yield of less than 98%).

For example, with an adsorbent according to the invention with a particle size of 0.54 mm, 1 m columns may be used and para-xylene may be produced in a yield of 98.5% or, with an adsorbent according to the invention with a particle size of 0.4 mm, 0.5 m columns may be used and para-xylene may be produced in a yield of 98.7%. For these tests, the pressure difference measured between the first and the last column is 3.4 bar (0.34 MPa) and 3.5 bar (0.35 MPa) respectively, which is less than or identical to the reference case.

In this example, it appears that the use of zeolite adsorbents according to the invention, i.e. the two adsorbents based on crystals of XPH type with a particle size (volume-average diameter) of 0.4 mm and 0.54 mm, make it possible to reduce the column length for the same flow rate of injected feedstock and purity/yield performance, which makes it possible to increase the production efficiency relative to conventional adsorbents (based on X crystals of conventional type); specifically, the production efficiency corresponds to the amount of para-xylene produced per unit of time and per bed volume.

TABLE 1

| | Adsorbent | | | | | |
|---|---|---|---|---|---|---|
| | A (comp) | A (comp) | A (comp) | A (comp) | A (inv) | A (inv) |
| Type of crystals | X | X | X | XPH | XPH | XPH |
| Volume-average diameter of the adsorbent (mm) | 0.4 | 0.54 | 0.7 | 0.7 | 0.4 | 0.54 |
| Column length (m) | 0.5 | 1 | 2 | 2 | 0.5 | 1 |
| Yield | 64.6% | 93.9% | 98.5% | 98.4% | 98.7% | 98.5% |

TABLE 1-continued

| | Adsorbent | | | | | |
|---|---|---|---|---|---|---|
| | A (comp) | A (comp) | A (comp) | A (comp) | A (inv) | A (inv) |
| Maximum rate (cm · sec$^{-1}$) | 1.6 | 1.5 | 1.3 | 1.4 | 1.8 | 1.5 |
| ΔP (MPa) | 0.31 | 0.34 | 0.35 | 0.37 | 0.35 | 0.34 |

The invention claimed is:

1. A zeolite adsorbent wherein:
   the zeolite adsorbent has a content of crystalline phase in the form of zeolite FAU of X type with hierarchical porosity of between 50% and 99% by weight, relative to the total mass of the adsorbent;
   the zeolite adsorbent has a content of barium ions (Ba$^{2+}$), expressed as barium oxide (BaO) of greater than 10% by weight relative to the total mass of the adsorbent;
   the zeolite adsorbent has a content of potassium ions (K$^+$), expressed as potassium oxide (K$_2$O), of less than 25% by weight relative to the total mass of the adsorbent;
   the zeolite adsorbent has a volume-average diameter of between 0.2 mm and 0.6 mm; and
   the zeolite adsorbent has sphericity characteristics such that:
      the zeolite adsorbent has a mean roundness of between 70% and 100%; and
      the zeolite adsorbent has a percentage of particles with an elongation of 0% of between 5% and 100%.

2. The zeolite adsorbent according to claim 1, wherein the zeolite adsorbent has an outer surface area, measured by nitrogen adsorption, greater than 20 m$^2$.g$^{-1}$.

3. The zeolite adsorbent according to claim 1, wherein the zeolite adsorbent has an outer surface area, measured by nitrogen adsorption, greater than 20 m$^2$.g$^{-1}$, and said outer surface area is associated with a population of mesopores with a mean diameter of between 2 nm and 50 nm.

4. The zeolite adsorbent according to claim 1, wherein the type X zeolite FAU with hierarchical porosity has an outer surface area, defined by the t-plot method from the nitrogen adsorption isotherm at a temperature of 77 K, after degassing under vacuum (P<6.7×10$^{-4}$ Pa), at a temperature of between 300° C. and 450° C. for a time ranging from 9 hours to 16 hours, of between 40 m$^2$.g$^{-1}$ and 400 m$^2$.g$^{-1}$.

5. The zeolite adsorbent according to claim 1, wherein the zeolite adsorbent comprises a binder, said binder comprising a clay or a mixture of clays selected from the group consisting of kaolins, kaolinites, nacrites, dickites, halloysites, attapulgites, sepiolites, montmorillonites, bentonites, illites and metakaolins, and also mixtures of two or more thereof in all proportions.

6. The zeolite adsorbent according to claim 1, wherein the percentage of particles with an elongation of less than 10% is between 50% and 100%.

7. The zeolite adsorbent according to claim 1, having a grain density of between 1.0 g.cm$^{-3}$ and 1.4 g.cm$^{-3}$, as measured by mercury intrusion (expressed relative to the dry mass of the zeolite adsorbent) and a total volume contained in macropores and mesopores (sum of the macropore volume and of the mesopore volume) measured by mercury intrusion, of between 0.20 cm$^3$.g$^{-1}$ and 0.40 cm$^3$.g$^{-1}$ (expressed relative to the anhydrous equivalent mass of the zeolite adsorbent).

8. The zeolite adsorbent according to claim 1, having a ratio (macropore volume)/(macropore volume+mesopore volume) of between 0.2 and 1.

9. A method of separating para-xylene from aromatic fractions containing 8 carbon atoms, comprising contacting an aromatic fraction containing 8 carbon atoms with at least one zeolite adsorbent according to claim 1.

10. A process for separating para-xylene from a mixture of C8 aromatic hydrocarbons, comprising contacting a mixture of C8 aromatic hydrocarbons with at least one zeolite adsorbent according to claim 1.

11. The process according to claim 10, wherein the process is performed in a simulated moving bed unit having the following characteristics:
 number of beds: 4 to 24; and
 number of zones: at least 4.

12. The process according to claim 10, which is conducted in the presence of a desorbent and wherein the process has a cycle time, corresponding to the time between two injections of the desorbent on a given bed, of between 4 and 18 minutes.

13. The process according to claim 10, wherein the process is worked at a temperature from 100° C. to 250° C., and at a pressure between the bubble pressure of xylenes at the process temperature and 3 MPa.

14. The process according to claim 10, which is conducted in the presence of a desorbent and wherein the process is operated to provide a ratio of the flow rates of the desorbent to a feedstock of between 0.7 and 2.5 and a recycle ratio of between 2 and 12.

15. The process according to claim 10, which is conducted in the presence of a desorbent and wherein the process is performed at a temperature of from 165° C. to 185° C. and wherein the water content in hydrocarbon-based effluents is adjusted to between 20 ppm and 150 ppm, by adding water to at least one of a feedstock comprising the fractions of aromatic hydrocarbon isomers containing 8 carbon atoms or the desorbent.

16. The process according to claim 10, which is conducted in the presence of a desorbent and wherein the desorbent is selected from the group consisting of toluene and para-diethylbenzene.

17. The zeolite adsorbent according to claim 1, wherein the content of crystalline phase in the form of zeolite FAU of X type with hierarchical porosity is between 80% and 98% by weight, relative to the total mass of the adsorbent.

18. The zeolite adsorbent according to claim 1, wherein the content of barium ions ($Ba^{2+}$), expressed as barium oxide (BaO) is greater than 23% by weight, relative to the total mass of the adsorbent.

19. The zeolite adsorbent according to claim 1, wherein the content of barium ions ($Ba^{2+}$), expressed as barium oxide (BaO) is between 23% and 42% by weight relative to the total weight of the adsorbent.

20. The zeolite adsorbent according to claim 1, wherein the zeolite adsorbent has sphericity characteristics such that:
 the zeolite adsorbent has a mean roundness of between 85% and 100%; and
 the zeolite adsorbent has a percentage of particles with an elongation of 0% of between 25% and 100%.

* * * * *